(12) United States Patent
Yamanaka et al.

(10) Patent No.: US 9,474,532 B2
(45) Date of Patent: Oct. 25, 2016

(54) EMBOLIZATION COIL

(75) Inventors: Yasushi Yamanaka, Kanagawa (JP); Atsushi Ogawa, Kanagawa (JP)

(73) Assignee: KANEKA CORPORATION, Osaka (JP)

( * ) Notice: Subject to any disclaimer, the term of this patent is extended or adjusted under 35 U.S.C. 154(b) by 386 days.

(21) Appl. No.: 13/394,806

(22) PCT Filed: Sep. 9, 2010

(86) PCT No.: PCT/JP2010/065513
§ 371 (c)(1),
(2), (4) Date: Mar. 7, 2012

(87) PCT Pub. No.: WO2011/030820
PCT Pub. Date: Mar. 17, 2011

(65) Prior Publication Data
US 2012/0172921 A1 Jul. 5, 2012

(30) Foreign Application Priority Data

Sep. 9, 2009 (JP) ................................. 2009-208737

(51) Int. Cl.
*A61F 2/01* (2006.01)
*A61B 17/12* (2006.01)
(52) U.S. Cl.
CPC ... *A61B 17/12022* (2013.01); *A61B 17/12109* (2013.01); *A61B 17/12145* (2013.01); *A61B 17/12154* (2013.01)
(58) Field of Classification Search
CPC ................................................ A61B 17/12154
USPC ................................................. 606/191, 200
See application file for complete search history.

(56) References Cited

U.S. PATENT DOCUMENTS

| | | | | |
|---|---|---|---|---|
| 7,608,089 | B2* | 10/2009 | Wallace | A61B 17/12113 606/200 |
| 8,613,282 | B2* | 12/2013 | Nikolchev | A61B 17/12022 128/830 |
| 2004/0199175 | A1* | 10/2004 | Jaeger et al. | 606/108 |
| 2005/0090856 | A1* | 4/2005 | Porter | 606/200 |
| 2006/0116708 | A1* | 6/2006 | Ogawa et al. | 606/200 |

(Continued)

FOREIGN PATENT DOCUMENTS

| | | |
|---|---|---|
| JP | 08-336600 | 12/1996 |
| JP | 09-108229 | 4/1997 |
| WO | 99/15116 | 4/1999 |

OTHER PUBLICATIONS

International Search Report for PCT/JP2010/065513 filed Sep. 9. 2010 in the name of Kaneka Corporation—English Translation.

*Primary Examiner* — Diane Yabut
(74) *Attorney, Agent, or Firm* — Birch, Stewart, Kolasch & Birch, LLP

(57) ABSTRACT

An embolic coil configured in such a manner that the risk that a stretch preventing wire breaks is very small even if the embolic coil is wound to a diameter smaller than the diameter of a secondary shape of the coil imparted thereto and also in such a manner that the embolic coil has excellent deliverability. An embolic coil is configured in such a manner that a stretch preventing wire and a coil, a part or the whole of said coil being coarsely wound, are affixed to each other at at least two different points. The portion of the stretch preventing wire which is located between the two different portions is provided with a portion to which a stretchable shape has been imparted.

6 Claims, 6 Drawing Sheets

(56) References Cited

U.S. PATENT DOCUMENTS

2007/0225738 A1* 9/2007 Pal .............................. 606/151
2008/0046093 A1* 2/2008 Davis et al. ............... 623/23.72
2010/0094395 A1* 4/2010 Kellett ............. A61B 17/12022
623/1.11

* cited by examiner

EMBOLIZATION COIL

CROSS REFERENCE TO RELATED APPLICATIONS

The present application is the U.S. national stage entry under 35 U.S.C. 371 of PCT International Patent Application Serial No. PCT/JP2010/065513 filed on Sep. 9, 2010 which claims the benefit of priority to Japanese Patent Application Serial No. 2009-208737 filed Sep. 9, 2009, which are hereby incorporated by reference.

TECHNICAL FIELD

The present invention relates to an embolization coil for use in intravascular treatment. More specifically, it relates to an embolization coil for use in treatment of cerebral aneurysm or embolism of blood vessel.

BACKGROUND ART

Currently, intravascular treatments such as those using catheter have been known as less-invasive treatment methods for intravascular lesions such as aneurysm. The embolization coil used for placement at a targeted site such as blood vessel or aneurysm in these intravascular treatment methods needs to show various characteristics such as those shown below.

First, the embolization coil should be flexible enough and show replacement efficiency in placement operation without damage by excessive load applied to the application site.

The embolization coil may be withdrawn and modified positionally and relocated after placement, and the embolization coil should have a function to prevent elongation then to the degree of more than its yielding point.

Various developments had been made to obtain these characteristics.

Examples of the developments include improvement of the placement efficiency of the embolization coil allowing rapid bending thereof when connected to the vascular wall, which is made possible by making the terminal of the embolization coil more flexible than the middle region, as disclosed in Patent Document 1, and provision of a function to prevent unlimited elongation of the embolization coil itself, which is made possible by installing an elongation-preventing member in the embolization coil, as disclosed in Patent Document 2.

However, even with such traditional technologies, there were still many problems to be studied, for example, for prevention of breakage of the elongation-preventing member (e.g., prevention of breakage when the coil is wound into a shape with a smaller diameter) and for improvement of the delivery efficiency of the embolization coil (efficiency in relocation of embolization coil in catheter and also in positional correction and relocation after withdrawal).

CITATION LIST

Patent Literature

Patent Document 1: JP-A No. 8-336600
Patent Document 2: JP-A No. 9-108229

SUMMARY OF INVENTION

Technical Problem

An object of the present invention is to provide an embolization coil with an elongation-preventing wire that is resistant to breakage even when the embolization coil is wound into a shape with a diameter smaller than that of the secondary shape thereof initially provided and has favorable delivery efficiency.

Solution to Problem

After intensive studies to achieve the object above, the inventors provides an embolization coil comprising an elongation-preventing wire and a partially or entirely pitch-wound coil that are fixed to each other at least two points different from each other, characterized in that the elongation-preventing wire has a region having an expandable/shrinkable shape in the region placed between the two points different from each other.

The phrase "fixed to each other at least two points different from each other" includes the cases where the coil and the elongation-preventing wire are fixed to each other directly and also where they are fixed to each other indirectly for example via the distal points of a pusher and the coil. In addition, the "two points different from each other" means two points separated in the axial direction when the coil is linear.

It is possible in this configuration to prevent breakage of the elongation-preventing wire when the coil has a pitch-wound region and to reduce deterioration in delivery efficiency caused by pitch winding by providing the elongation-preventing wire with an expandable/shrinkable shape.

The "pitch-wound coil," as used herein, means a coil having a region where the neighboring wire rods forming the coil are wound not in contact with each other, there is an opening between the neighboring wire rods, and the size of the opening is 5% or more of the width of the wire rod.

Also provided is the embolization coil, wherein the coil has a pitch-wound region and a densely wound region. In particular, when the coil has both a pitch-wound region and a densely wound region, it is possible to obtain more favorable delivery efficiency than a coil having only a pitch-wound coil (i.e., it is possible to obtain both sufficient resistance to breakage of the elongation-preventing wire and favorable delivery efficiency easily).

The "densely wound coil" means a coil in which the neighboring wire rods forming the coil are wound in contact with each other or in which there is an opening between the neighboring wire rods and the size of the opening is less than 5% of the width of the wire rod.

Also provided is the embolization coil wherein the natural length of the region of the coil placed between the two points different from each other (the natural length is the length in the axial direction when the embolization coil is placed still in a linear groove without any force applied in the axial direction) is larger than the natural length of the region placed between the two points of the elongation-preventing wire different from each other. It is possible in this way to reduce the fatigue breakage caused for example by stress concentration in the elongation-preventing wire more efficiently by bringing the natural lengths of the coil and the elongation-preventing wire in particular regions into such a particular relationship.

Also provided is the embolization coil, wherein the region having an expandable/shrinkable shape in the elongation-preventing wire is placed between the two points different from each other, as it is expanded in the coil axial direction. It is possible to reduce the fatigue breakage caused for example by stress concentration in the elongation-preventing wire more efficiently, especially by placing the elongation-preventing wire into the coil as it is elongated.

Also provided is the embolization coil, wherein the region having an expandable/shrinkable shape in the elongation-preventing wire has a periodic shape. It is possible to improve the delivery efficiency of the embolization coil more effectively and reliably, particularly when the region having an expandable/shrinkable shape in the elongation-preventing wire has a periodic shape.

Also provided is the embolization coil, wherein the pitch-wound region of the coil is placed partially in the proximal region of the coil.

Also provided is the embolization coil, wherein the maximum expandable length of the region of the elongation-preventing wire placed between the two points different from each other is 130% or less with respect to the natural length (100%) of the region of the coil placed between the two points different from each other.

Also provided is the embolization coil, wherein the length of the pitch-wound region in the region of the coil placed the two points different from each other is 5 to 40% of the natural length of the region of the coil placed between the two points different from each other.

Also provided is the embolization coil, wherein the region of the elongation-preventing wire having an expandable/shrinkable shape is formed by twisting two or more wires.

Advantageous Effects of Invention

The present invention provides a superior embolization coil resistant to breakage of the elongation-preventing wire thereof. The present invention also provides an embolization coil resistant to deterioration in delivery efficiency.

DESCRIPTION OF EMBODIMENTS

The present invention relates to an embolization coil comprising an elongation-preventing wire and a partially or entirely pitch-wound coil fixed to each other at least two points different from each other, characterized in that the elongation-preventing wire has a region having an expandable/shrinkable shape in the region placed between the two points different from each other.

Figure 1:
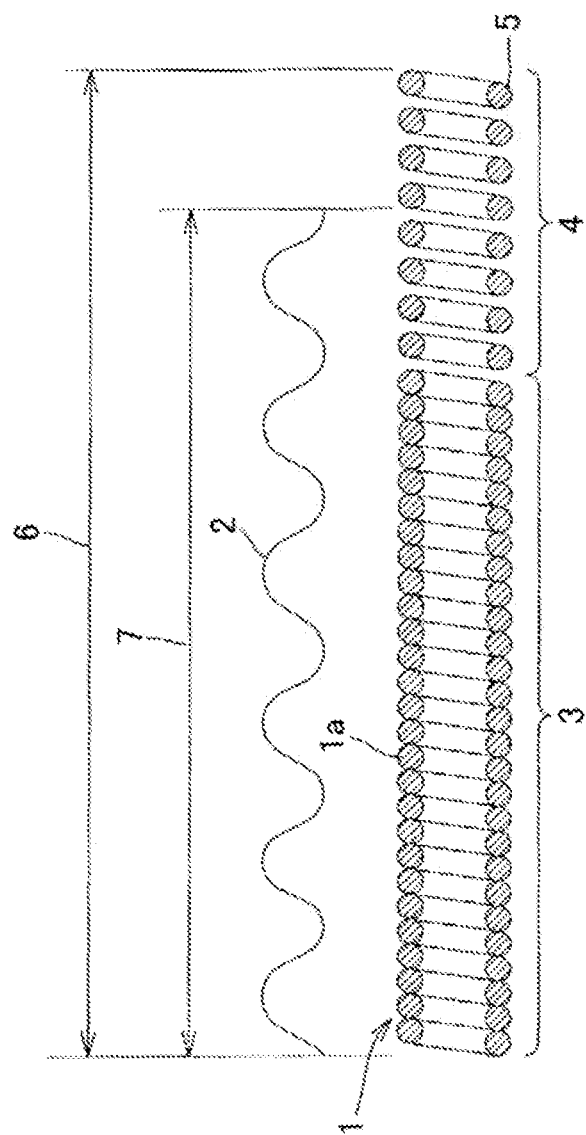
FIG. 1 is an exploded cross-sectional view separately illustrating a coil 1 and an elongation-preventing wire 2 constituting an embodiment of the embolization coil of the present invention.

FIG. 1 is an exploded cross-sectional view illustrating an example of the constituent parts, a coil and an elongation-preventing wire, of the embolization coil of to the present invention. The coil 1 has a primary shape in which the wire rod 1*a* is wound, having a pitch-wound region 4 placed to the proximal side 5 and a densely wound region 3 to the distal side of the coil 1. The proximal side of the coil is the side of the coil placed closer to the surgeon during treatment. The elongation-preventing wire 2 has a periodic wave-shaped expandable/shrinkable shape over the entire length.

Also in the example of FIG. 1, the natural length 6 of the coil 1 is longer than the natural length 7 of the elongation-preventing wire 2. Thus, when the terminals of the coil 1 and the elongation-preventing wire 2 are chosen for example as the two points different from each other and fixed to each other directly or indirectly at the terminals of the coil 1, the natural length 6 of the region of the coil 1 placed between the two points different from each other is longer than the natural length 7 of the region of the elongation-preventing wire 2 placed between the two points different from each other. In this case, the coil 1 contains the pitch-wound region between the two points and the elongation-preventing wire 2 contains the region having an expandable/shrinkable shape between the two points.

In the present invention, the coil and the elongation-preventing wire are only needed to be fixed to each other at two points different in the axial direction, when the coil is linear and, as described in the description on FIG. 1 above, they are not needed to be fixed at the terminals of the coil and the elongation-preventing wire. Specifically, any two points on the coil separated in the axial direction may be chosen; any two points on the elongation-preventing wire separated in the axial direction may be chosen; and they are fixed to each other at the respective two points in the corresponding axial directions. For example, when the relationship between the natural length of coil and that of the elongation-preventing wire at the region placed between the two points is in the particular relationship described above, it is possible to obtain the advantageous effects of the present invention more favorably. Thus, the configuration of the regions of the coil and the elongation-preventing wire outside the region between the two points is arbitrarily determined, if the advantageous effects of the present invention are not impaired.

Figure 2:
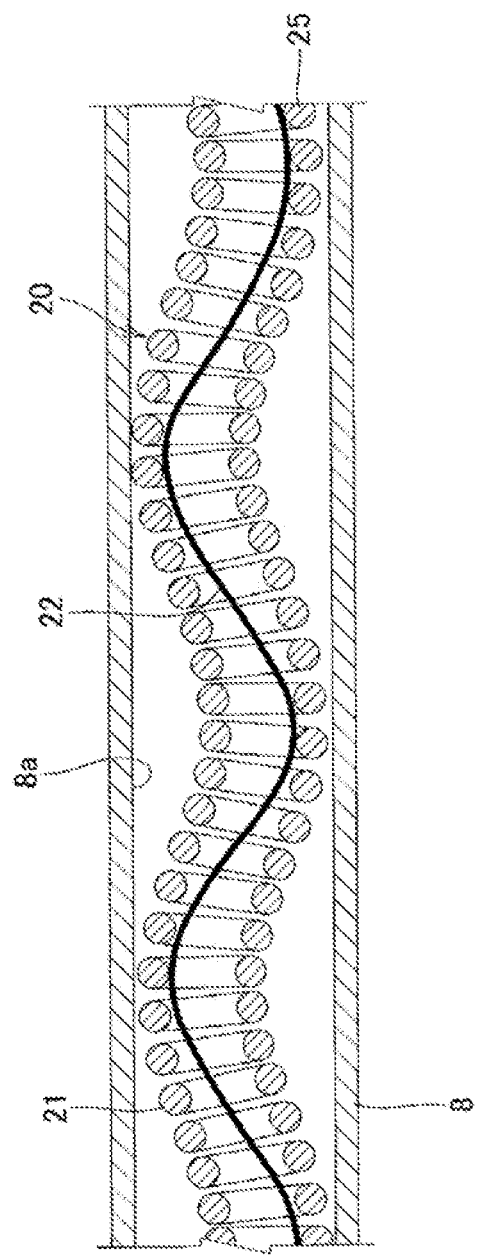
FIG. 2 is a schematic view illustrating the kink-like symptom of a conventional embolization coil that may occur because of the loosening of the elongation-preventing wire when the coil is pitch-wound.

In the present invention, it is possible, as described above, to reduce the risk of breakage of the elongation-preventing wire, even when it is wound into a shape with a smaller diameter because the coil is pitch-wound partially or entirely. However, in the case of a conventional embolization coil having an elongation-preventing wire not in the expandable shape, if the coil is pitch-wound partially or entirely and for example when force is applied to the coil in the axial direction for dislocation of the embolization coil in catheter, the embolization coil 20 may be bent in the catheter 8, leading to relaxation of the elongation-preventing wire 22 in the coil 21, as shown in FIG. 2. The relaxation causes a problem of the coil 21 being brought into a kink-like state.

Figure 3:
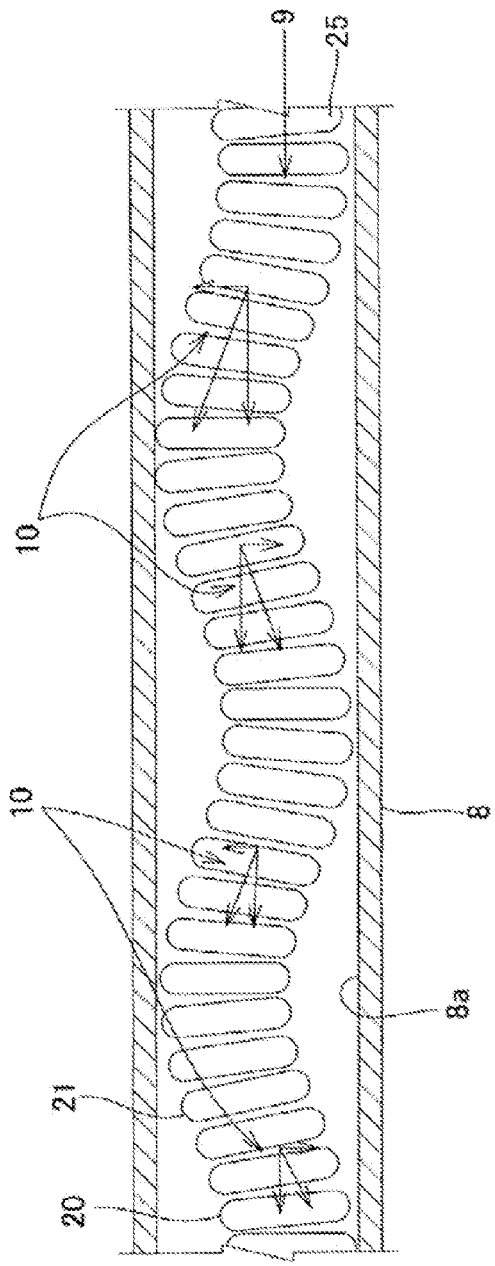
FIG. 3 is a schematic view illustrating the stresses generated in the coil by the elongation-preventing wire in the state of the embolization coil shown in FIG. 2.

FIG. 3 is a drawing showing the stresses generated in the coil by the elongation-preventing wire in the state of the embolization coil shown in FIG. 2. As shown in FIG. 3, when force 9 is applied from the proximal end 25 of the coil 21 in the coil axial direction (lengthwise direction of catheter 8 in FIG. 3), the elongation-preventing wire relaxed in the coil 21 (not shown) generates force vectors 10, as the force is dispersed in the coil axial direction and also in the radial direction (in FIG. 3, forces in the lengthwise and radial directions of the catheter 8). The stress generates a force to press the coil 21 onto the internal wall face 8*a* of the catheter 8 (hereinafter, referred to as external wall) in the region of coil 21 in contact with the internal wall face 8a (external wall), thus leading to significant decrease of the delivery efficiency.

In contrast, in the case of the embolization coil of the present invention, which has an elongation-preventing wire formed in the expandable/shrinkable shape, when the coil having a pitch-wound region is compressed, the expandable/shrinkable shape is bent in each of the regions in the coil, leading to dispersion of the force pressing it onto the internal wall face (external wall) of the material surrounding outer surface of the coil such as catheter and thus eliminating the decrease in delivery efficiency.

The expandable/shrinkable shape, as used herein, is a structure such as wave shape or spiral shape, in which, when force is applied in the axial direction of the embolization coil, the force is transmitted less efficiently in the axial direction and more efficiently in the radial direction (direction perpendicular to the axial direction), as it is dispersed.

Hereinafter, each unit for use in the present invention will be described.

The coil for use in the present invention is partially or entirely pitch-wound, and it is thus possible to compress the coil before expansion of the elongation-preventing wire and to prevent the risk of breakage the elongation-preventing wire. For example, when an embolization coil is inserted into an aneurysm having a diameter smaller than the secondary shape of the coil (generally, an embolization coil has a primary coil shape forming the coil and a secondary coil shape macroscopically formed by the coil itself as wire rod) the elongation-preventing wire is easily placed along the aneurysnial wall in the coil. For that reason, there is a possibility that the elongation-preventing wire may become insufficient in length and broken as it is stretched, when the embolization coil is inserted into aneurysm from the distal region finally to the coil proximal region thereof. However, in the structure above, the pitch-wound region of the coil shrinks, compensating the insufficiency of the elongation-preventing wire and thus preventing breakage thereof.

The partially or entirely pitch-wound coil may be prepared by forming the pitch-wound region in the stage of coiling a particular wire rod, but may be prepared by forming a densely wound coil and forming a pitch-wound region therein by elongating any region thereof in the axial direction. It is also possible to obtain the advantageous effect of preventing breakage of the elongation-preventing wire more reliably, by making the pitch distance of the pitch-wound region 5% or more, more preferably 20% or more, with respect to the external diameter of the wire rod forming the coil. Since the delivery efficiency of an embolization coil tends to decrease by increase in coil pitch distance, the pitch distance is preferably not larger than 40% with respect to the external diameter of the wire rod.

The "pitch distance," as used in the present invention, means the distance between neighboring wire rods in the pitch-wound region of the coil. The distance between wire rods may be uniform over the entire pitch-wound region or may be altered as needed.

The coil for use in the present invention may be pitch-wound over the entire region, but it is preferable to make the coil have both a pitch-wound region and a densely wound region for prevention of undesirable compression during delivery and deterioration in delivery efficiency. In particular, in an embolization coil having a secondary shape, it is preferable to pitch-wind a region in the coil proximal region (the coil proximal region is a region of the coil placed to the surgeon side during treatment) where the elongation-preventing wire may become insufficient when an embolization coil having a large secondary diameter is wound into a shape with a smaller diameter.

The proportion of the coil pitch-wound region in the region placed between the two points different from each other is preferably 5 to 40% with respect to the natural length of the region of the coil placed between the two points different from each other. It is possible to prevent breakage of the elongation-preventing wire and also to reduce deterioration in delivery efficiency more efficiently by forming a needed length of pitch-wound region only partially in the coil, as described above.

The coil for use in the present invention preferably has a primary coil shape having a lumen formed therein by winding a wire rod and a secondary coil shape formed by winding the primary coil as wire rod. The secondary coil shapes include various two-dimensional shapes and three-dimensional shapes such as helical structure. A three-dimensional shape is particularly preferable, because it easily occupies a space of a particular volume or more without aggregation during placement in the blood vessel.

The coil for use in the present invention can be prepared from various raw materials that are biocompatible, such as metal wires and resins, but particularly preferable is use of a metal wire which is stable in its 3D-shape (in particular, a metal coil in which a metal wire is wound helically). Examples of materials for the biocompatible metal wire include platinum, tungsten, titanium, gold, iridium, palladium, tantalum, and the alloys thereof, stainless steel and the like. In particular, a metal wire of platinum or a platinum alloy is preferable. Heads placed in the distal region of the coil can also be prepared similarly from the metals and resins above.

The elongation-preventing wire for use in the present invention has an expandable/shrinkable shape. It was thus possible to eliminate the deterioration in delivery efficiency caused by pitch winding (i.e., when the elongation-preventing wire placed inside the coil is has a region in the expandable/shrinkable shape and the coil having a pitch-wound region is compressed, the elongation-preventing wire is effective in dispersing the force pressing the coil to the external wall, which is caused by relaxation of the wire and can eliminate deterioration in delivery efficiency). The expandable/shrinkable shape may be provided to the entire elongation-preventing wire or to the entire or partial region placed between the two points different from each other.

The expandable/shrinkable shape of the elongation-preventing wire is not particularly limited, and may be a periodic or non-periodic random shape, if the wire can vary in shape between the elongated and shrunk states. It is preferably a periodic shape, such as wave-like shape or spiral shape for more effective and reliable improvement of the delivery efficiency of the embolization coil. The wave-like or spiral shapes include two-dimensional and three-dimensional shapes. For example, as for the shape in each cycle, one wave shape or multiple wave shapes may be contained in one cycle, if the shape is a two-dimensional wave shape. When multiple wave shapes are contained in one cycle, the widths (amplitudes) and the wavelengths of the wave shapes in one cycle may be different from each other. In addition, the shapes in each cycle may not be completely identical with and may be slightly deformed from each other.

The degree of "expandability/shrinkability" is not particularly limited, but the length of elongation-preventing wire can be elongated preferably to 105% or more, more preferably 110% or more, and still more preferably 120% or more, with respect to 100% of the natural length of the region placed between the two points of the elongation-preventing wire different from each other.

Figure 4:
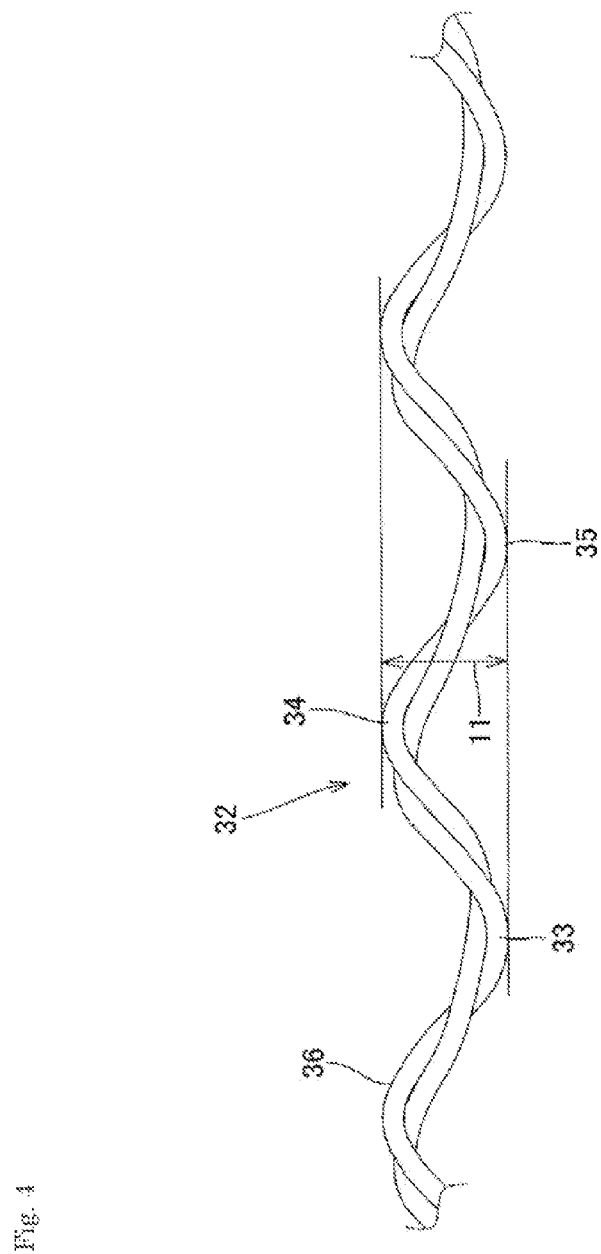
FIG. 4 a partially expanded view of an expansion-preventing wire in an expandable/shrinkable shape in an embodiment of the embolization coil of the present invention.

The maximal width of the expandable/shrinkable shape is not particularly limited and arbitrary, if the advantageous effects of the present invention are obtained, independently of whether the shape is a periodic shape or a non-periodic random shape. However, the width (maximal width) of the expandable/shrinkable shape provided to the elongation-preventing wire in the state when the coil and the elongation-preventing wire are not connected to each other is preferably not larger than the internal diameter of the lumen region of the coil (primary coil). As shown in FIG. 4, the elongation-preventing wire 32 of a twisted wire 36 prepared by twisting the wires as will described below is provided with a periodic two-dimensional wave shape as the expandable/shrinkable shape. The width (maximal width) of the provided periodic shape corresponds to the region indicated by code number 11. In the case of the elongation-preventing wire 32 shown in FIG. 4 for example, the series of the regions of the twisted wire from valley 33, via mountain 34 to valley 35 constitutes one cycle.

As described above, when the width of the periodic shape is not larger than the internal diameter of the primary coil, it is possible to improve the delivery efficiency of the embolization coil more effectively and reliably.

The length of one cycle of the periodic shape is preferably 100 μm or more and 10 mm or less, more preferably 200 μm or more and 500 μm or less. When the length of one cycle is more than 10 mm, there is fewer number of stress-distributing positions, possibly leading to deterioration in delivery efficiency, while when it is less than 100 μm, the wire rod is bent at an sharp angle, possibly leading to deterioration of the strength of the wire rod.

In addition, the region having an expandable/shrinkable shape in the elongation-preventing wire may not necessarily be formed with one wire rod, and it is possible to fold one wire multiple times between different two points (i.e., integrated wire having wires at a number identical with the number of folding) before fixation to the coil.

The elongation-preventing wire for use in the present invention may be a twisted wire prepared by twisting two or more wires. When two or more, wires are twisted, the twisting interval is preferably 2 to 100 times larger than the diameter of the twisted wire. Even in the range above, it is possible to make the two or more wires resistant to become loosened especially by wining the wire densely and to reduce the risk of the two or more wires being separated during processing of the elongation-preventing wire into the expandable/shrinkable shape.

Figure 5:
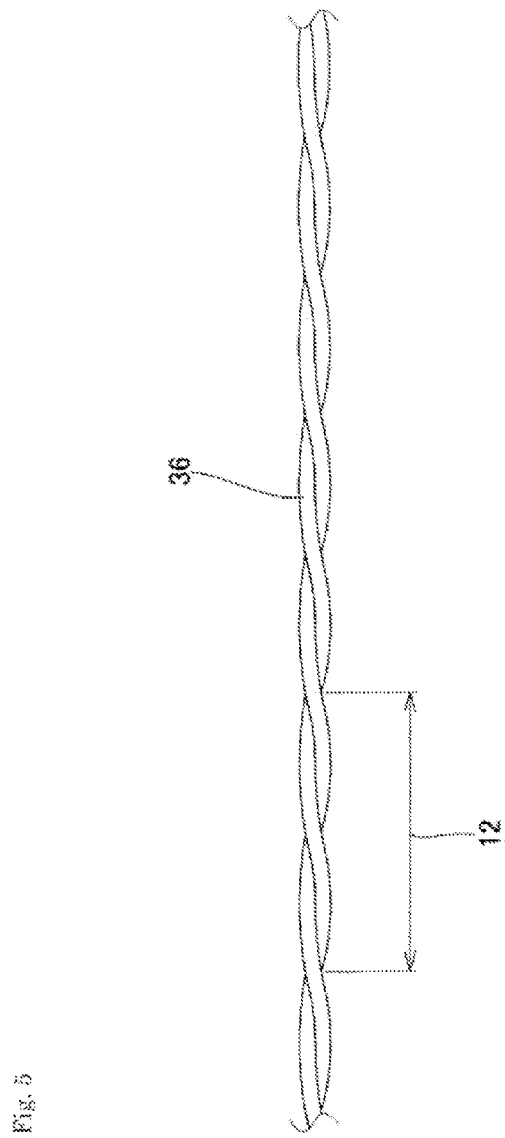
FIG. 5 is a partial side view of an elongation-preventing wire formed by winding of two or more wires.

For example, as shown in FIG. 5, in the case of a twisted wire 36 formed by twisting two wires, the twisting interval, which corresponds to the region indicated by code number 12, is the distance of the region where the wires are wound in one cycle. Similarly, in the case of three or more wires, it is also the distance of the region where the wires are wound in one cycle. FIG. 5 is a view showing a twisted wire of two wires that is expanded for clear understanding of the twisting interval.

It is possible, by providing the twisted wire 36 shown in FIG. 5 with a periodic shape, to obtain an elongation-preventing wire 32 provided with a periodic wave shape similar to that shown in FIG. 4.

In the embolization coil of the present invention, the natural length of the region of the coil placed between the two points different from each other is preferably longer than the natural length of the region of the elongation-preventing wire placed between the two points different from each other. It is thus possible to fix the expandable/shrinkable elongation-preventing wire placed between the two points to the coil, as it has a force compressed in the axial direction and to reduce the load by metal fatigue applied to the elongation-preventing wire, which is caused by repeated bending during positional correction and relocation needed during placement of the embolization coil.

In particular, to obtain such an effect more effectively, the natural length of the region of coil placed between the two points different from each other is preferably more than 100% and 130% or less with respect to 100% of the natural length of the region of the elongation-preventing wire placed between the two points different from each other.

As described above, the coil and the elongation-preventing wire may have such a relationship in length over their entire lengths or only over a region between particular two points.

In the present invention, when they have such a particular relationship in length, a particular region of the elongation-preventing wire is preferably placed between the two points different from each other, as it is expanded in the axial direction of the coil.

The method of fixing the coil and the elongation-preventing wire to each other in such a configuration is not particularly limited, but they can be fixed to each other, for example, by a method of fixing the elongation-preventing wire, as the coil is compressed, or by a method of fixing it as the elongation-preventing wire is stretched. It is also favorable to adjust the strength of the expandability/shrinkability of the elongation-preventing wire and the coil properly in such a manner that the elongation-preventing wire is kept in the embolization coil as it is elongated.

In addition, the maximum expandable length of the region having an expandable/shrinkable shape in the elongation-preventing wire is preferably 130% or less with respect to the natural length (100%) of the region of the coil placed between the two points different from each other, for prevention of the coil plastic deformation of the elongation-preventing wire. The "maximum expandable length" is the length of the region of an elongation-preventing wire between two points different from each other when the region of the elongation-preventing wire breaks, as it is elongated in the axial direction.

The elongation-preventing wire for use in the present invention can be prepared, similarly to the coil above, from various raw materials that are biocompatible, such as metal wires and resin wires, but particularly preferable is use of a metal wire, which is stable in its 3D-shape. Examples of the materials for the biocompatible metal wire include platinum, tungsten, titanium, gold, iridium, palladium, tantalum, and the alloys thereof, stainless steel and the like. In particular, a metal wire of platinum or a platinum alloy is preferable.

Figure 6:
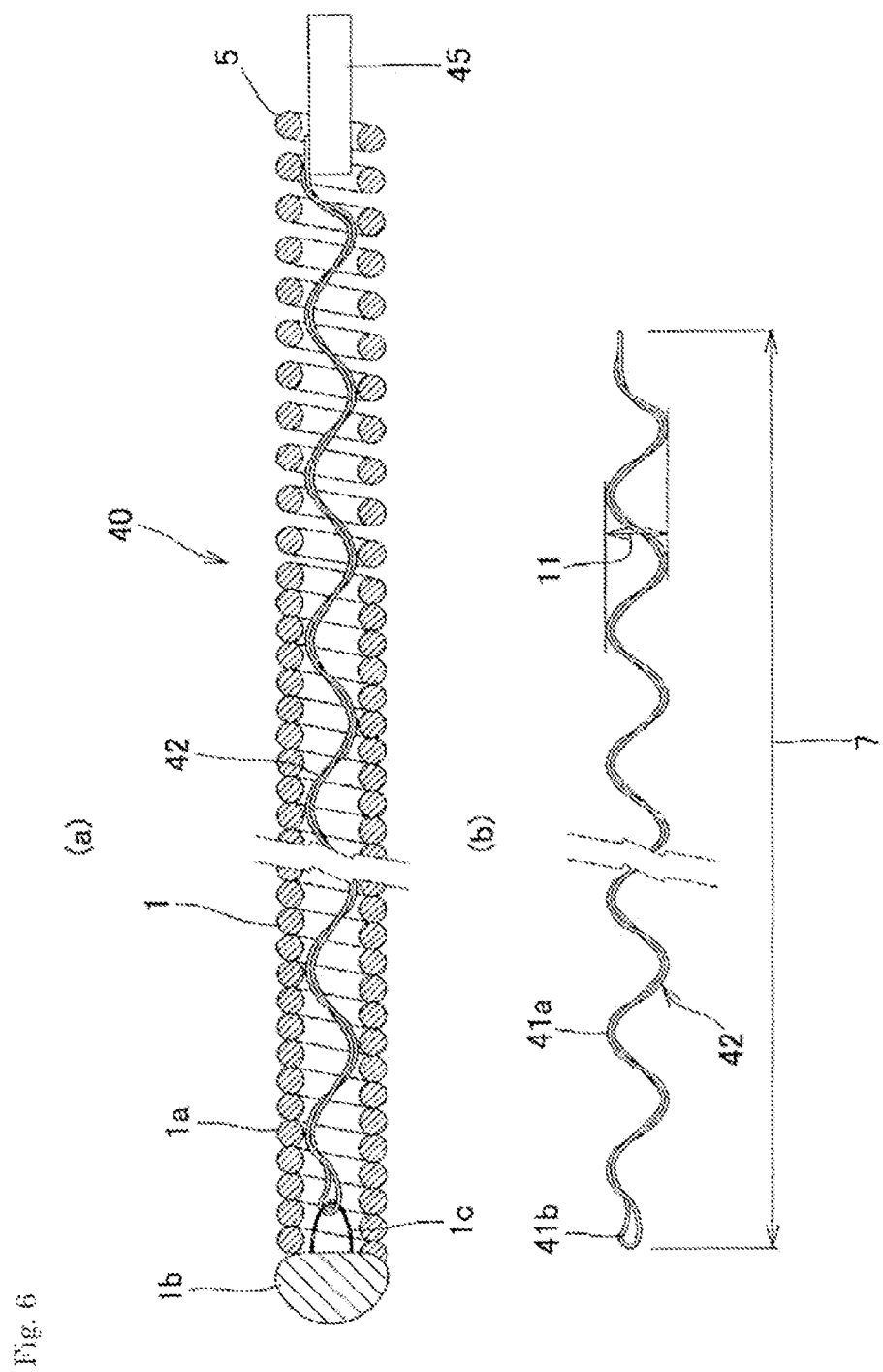
FIGS. 6(*a*) and 6(*b*) are cross-sectional views illustrating the embolization coil used in Example 1 and an elongation-preventing wire before fixation to the coil respectively.

A favorable example of the embolization coil of the present invention will be described briefly with reference to FIG. 6. The coil 1 constituting the embolization coil 40 in the present Example has a structure similar to that of the coil shown in FIG. 1 (the same code numbers are allocated to the same components and description on the same components is omitted). The difference is that a mostly hemispherical head 1b is formed for prevention of severe friction in catheter and damage to the vascular wall and a first loop is projecting toward coil proximal side 5 in the lumen of the coil 1 of the head 1b is formed. Alternatively, the elongation-preventing wire 42 has a second loop 41b made of a wire 41a in the distal region and additionally a region other than the second loop 41b that is made of a twisted wire prepared by twisting wires 41a, and has a periodic wave-like shape at a particular amplitude 11 over the entire length. Although a single wire 41a is used in this embodiment, a twisted wire of multiple wires may be used in another embodiment.

The coil 1 and the elongation-preventing wire 42 are fixed to each other in the distal region, as the first loop is and the second loop 41b are inserted to each other. Alternatively in the proximal region 5 of the coil, they are directly bound to each other by welding or by use of an adhesive or indirectly via a connecting member 45. The connecting member 45 for use may be any conventional connecting member.

FIG. 6(b) shows a elongation-preventing wire 42 before fixation and code number 7 indicates its natural length. FIG. 6(a) shows the cross section of the embolization coil 40 after assembly, and the elongation-preventing wire 42 in FIG. 6(a) is placed, as the coil is extended in the axial direction.

Such an embolization coil can be used favorably in intravascular treatment, for example, of cerebral aneurysm and embolism of the blood vessel.

EXAMPLES

Hereinafter, Examples and Comparative Examples conducted to Confirm the operational advantages of the embolization coil of the present invention will be described.

Example 1

A metal coil made of a platinum-tungsten alloy wire (wire rod external diameter: 45 μm) having a coil internal diameter of 150 μm and a natural length of 200 mm was used. A pitch-wound region having a gap distance of 30% of the external diameter of the wire rod was formed in the proximal 30 mm region of the coil and a densely wound region in the other region. The rate of the pitch-wound region was 15%. A wire rod (twisted wire) of a platinum-tungsten alloy wire having a natural length of 195 mm in a wave shape at an amplitude of 100 μm was used as the expandable/shrinkable elongation-preventing wire. The maximum expandable length of the region placed between the following two points of the elongation-preventing wire was 115% with respect to the natural length of the region. The elongation-preventing wire was placed between the terminal two points of the coil, as it is elongated to a length of 200 mm, to give an embolization coil in a spiral secondary shape having a diameter of 16 mm. FIG. 6 shows the cross-sectional view of the embolization coil used, in Example 1 and the elongation-preventing wire before fixation to the coil.

Comparative Example 1

A metal coil made of a platinum-tungsten alloy wire (wire rod external diameter: 45 μm) having a coil internal diameter of 150 μm and a natural length of 200 mm was used. A pitch-wound region having a gap distance of 30% of the external diameter of the wire rod was formed in the proximal 30 mm region of the coil and a densely wound region in the other region. The rate of the pitch-wound region was 15%. A linear elongation-preventing wire of a platinum-tungsten alloy wire having a natural length of 200 mm was placed between the two terminal points of the coil, to give an embolization coil in a spiral secondary shape having a diameter of 16 mm. The maximum expandable length of the region placed between the two points of the elongation-preventing wire described above was 100% with respect to the natural length of the region.

Comparative Example 2

A metal coil made of a platinum-tungsten alloy wire (wire rod external diameter: 45 μm) consisting of a densely wound region over the entire length and having a coil internal diameter of 150 μm and natural length of 200 mm was used. A linear elongation-preventing wire of a platinum-tungsten alloy wire having a natural length of 200 mm was placed between the two terminal points of the coil, to give an embolization coil in a spiral secondary shape having a diameter of 16 mm. The maximum expandable length of the region placed between the two points of the elongation-preventing wire described above was 100% with respect to the natural length of the region.

Each of the samples prepared in the Example and Comparative Examples 1 and 2 was placed in an aneurysm model of silicone (diameter; 4 mm) and then withdrawn, and breakage of the elongation-preventing wire was examined. In addition, each of the samples obtained in the Example and Comparative Examples 1 and 2 was reciprocated five times in a catheter; the force applied to the hand then was measured with a force gauge; and the average was used as the lubricity indicator. When the value of the lubricity indicator is lower, the delivery efficiency is better. The results are summarized in Table 1.

The phrase "reciprocated five times in a catheter" specifically means the followings: A sample is placed in a common microcatheter in such a manner that the distal terminal of the sample is located at a position approximately 10 cm backward from the distal opening of the catheter; the sample is pushed forward from the position until the approximately 10 cm region of the sample from the distal end extends out of the distal opening of the microcatheter (as the proximal-sided region of the sample remained in the catheter); the sample is pulled backward until the distal terminal of the sample is placed in the catheter approximately 10 cm proximal from the distal opening of the microcatheter. The series of operations was repeated five times as unit reciprocation.

The "average" means the average of five maximum values obtained in the repeated reciprocal operations above.

TABLE 1

|  | Example 1 | Comparative Example 1 | Comparative Example 2 |
|---|---|---|---|
| Elongation-preventing wire after placement in aneurysm model | not broken | not broken | broken |
| Lubricity indicator (N) | 0.35 | 0.67 | 0.32 |

REFERENCE SIGNS LIST

1 Coil
2 Elongation-preventing wire
3 Densely wound region
4 Pitch-wound region
5 Coil the proximal side
6 Natural length of coil before fixation
7 Natural length of elongation-preventing wire before fixation
8 Catheter
9 Force in the coil axial direction
10 Vector of force
11 Width of elongation-preventing wire in periodic shape
12 Twisting interval of elongation-preventing wire

The invention claimed is:

1. An embolization coil comprising:
   a placement coil having both of a pitch-wound region and a densely wound region to be placed in a body; and
   an elongation-preventing wire provided in the placement coil fixed to said placement coil at, at least, two points different from each other, wherein
   the pitch-wound region of the coil is placed in at least an end portion of a proximal region of the coil,
   the elongation-preventing wire has a region having an expandable/shrinkable shape in the region placed between the two points different from each other,
   the region having the expandable/shrinkable shape has a periodic shape,
   the elongation-preventing wire is formed by twisting wires of platinum-tungsten alloy,
   the periodic shape is two-dimensional or three-dimensional shape selected from the group consisting of a wave shape and a spiral shape, being provided over the entire length of the elongation-preventing wire,
   a natural length of the region of the coil placed between the two points different from each other is longer than 100% and 130% or less with respect to 100% of the natural length of the region of the elongation-preventing wire placed between the two points different from each other,
   a maximum expandable length of the region of the elongation-preventing wire placed between the two points different from each other is 130% or less with respect to the natural length (100%) of the region of the coil placed between the two points different from each other,
   a length of the pitch-wound region in the region of the coil placed between the two points different from each other is 5 to 40% of the natural length of the region of the coil placed between the two points different from each other, and
   the region having an expandable/shrinkable shape in the elongation-preventing wire is placed between the two points different from each other, so that the elongation-preventing wire is expanded from its natural length in the coil axial direction.

2. The embolization coil according to claim 1, wherein the maximal width of the expandable/shrinkable shape of the elongation preventing wire is not larger than the internal diameter of the coil in the state before the coil and the elongation-preventing wire are fixed to each other.

3. The embolization coil according to claim 1, wherein the pitch wound region of the coil is placed partially in the proximal region of the coil.

4. The embolization coil according to claim 3, wherein the pitch-wound region of the coil is disposed partially only from an end of the proximal region of the coil to a distal region of the coil.

5. The embolization coil according to claim 1, wherein the region of the elongation-preventing wire having an expandable/shrinkable shape is formed by twisting two or more wires.

6. The embolization coil according to claim 1, wherein the elongation-preventing wire is fixed to the placement coil so that the placement coil is compressed by a compressive force created by the elongation-preventing wire.

* * * * *